United States Patent [19]

Revel et al.

[11] Patent Number: 5,358,867
[45] Date of Patent: Oct. 25, 1994

[54] **DNA CLONING AND EXPRESSION OF AN L7 PROTEIN WHICH MODULATES THE 2′-5′ OLIGOSYNTHETASE AND H2-K*K RESPONSE TO TYPE-I INTERFERON**

[75] Inventors: Michel Revel; Lester Shulmann, both of Rehovot, Israel; Marc Fellous, Paris, France

[73] Assignee: Yeda Research and Development Co. Ltd., Rehovot, Israel

[21] Appl. No.: 120,030

[22] Filed: Sep. 13, 1993

Related U.S. Application Data

[63] Continuation of Ser. No. 436,332, Nov. 14, 1989, abandoned.

[30] Foreign Application Priority Data

Nov. 14, 1988 [IL] Israel ......................................... 88377

[51] Int. Cl.$^5$ ...................... A61K 37/66; C12P 21/06; C12N 15/00; C07H 17/00
[52] U.S. Cl. ............................... 435/240.2; 435/320.1; 435/69.52; 530/351; 424/85.4; 536/23.52
[58] Field of Search .................. 435/69.5, 69.51, 69.52, 435/320.1, 240.2, 572.3; 530/351; 424/85.4, 85.5, 85.6, 85.7; 536/23.52

[56] References Cited

U.S. PATENT DOCUMENTS 4,808,523 2/1989 Revel.

OTHER PUBLICATIONS

Langer et al., "Interferon receptors", *Immunology Today*, vol. 9, No. 12 (1988), pp. 393–401.
Radziuddin et al., "Receptors for human α and β interferon but not for η interferon are specified by human chromosome 21", *Proc. Natl. Acad. Sci. USA*, vol. 81 (Sep. 1984) pp. 5504–5508.
Traub, "Purfication and Properties of the α-Interferon Receptor of Human Lymphoblastoid (Namalva Cells)," *J. Biological Chemistry*, vol. 259, No. 22 (Nov. 25, 1984) pp. 13872–13877.
Zhang, "The Isolation of Human β-Interferon Receptor by Wheat Germ Lectin Affinity and Immunosobent Column Chromatographies", *J. Biological Chemistry*, vol. 261, No. 17, (Jun. 15, 1986), pp. 8017–8021.
Yonehara, S. et al., "Monoclonal Anti–Idiotype Antibody for Anti–Human Interferon-α that Compete with Interferon-α in Binding to Human Cell Surface and Inhibit the Interferon Action," in The Biology of the Interferon System 1985: Proceedings of the 1985 TNO–ISIR Meeting on the Interferon System, Held in Clearwater Beach, Florida, USA on 13–18 Oct., 1985, Steward, W. E. et al., Eds., Elsevier Science, Amsterdam, 1986.
Yonehara et al, Biol. Interferon Syst. Proc. TNO–ISIR Meet. Interferon Syst. 4th (1986) pp. 167–171 (see abstract).
Aguet et al, Cell 55: 273–280 (1988) "Molecular Cloning and Expressing of the human IFN-γ receptor".
Langer Biochem. and Biophysical Research Comm. pp. 1264–1270 Radiolabeling the IFN-α receptor.
Suggs et al, PNAS 75:2746–2749 (1978) "Immunological Screening of method of detect specific . . . ".

*Primary Examiner*—David L. Lacey
*Assistant Examiner*—T. Michael Nizbet
*Attorney, Agent, or Firm*—Browdy and Neimark

[57] ABSTRACT

The gene encoding a protein (L7) which appears to be a part of the human Type I interferon receptor has been cloned and expressed by recombinant DNA techniques. The protein imparts a non-species specific enhanced responsiveness to Type I interferon to transformed cells. The protein is found on the surface of Daudi cells and has structural features characteristic of receptor proteins.

6 Claims, 9 Drawing Sheets

FIG. 1(a)

SEQUENCE OF TYPE I INTERFERON RECEPTOR COMPONENT CDNA CLONE L7

```
                              31                                              61
AAT TCT GAG AAG AGT GGC TGC TCA GCC CAT TTC CCC GGC CTA AGT TTG GGA GGC CCC TCA
                              91                                             121
AGC CCC CAT CTT ACA GCT CGC ACC AGC AGT CTA GGG GAG GAG CGG ACA GCA GTG ACT CTC
                             151                                             181
AGG ACA GCC AGC AGA TGG ACG CCT ATG TCC CCA GGC ATG AGC TCT GCC TGT CAG ACC CTG
                             211                                             241
GAT TGG AAC CTC CAG TGT ACG TGC CTC CGC CCT CAT ACA GAT CGC CCC CGC AGA ACA TCC
                             271                                             301
CAA ACC CCT ACT TGG AAG ACA CGG TGC CCA TAA ATG TGT GTG GCG GTC ACA GTC AAC AGC
                             331                                             361
AGT CTC CGA CCG AGA AGG CTG GGG CCA GCG GTC AGC CTC CTT CAG GCC CCC CTG GAA CTG
                             391                                             421
GGA ATG AGT ATG GTG TGA GCC CCC GCT TGC CTC AGG GGC TCC CCG CAC ATC CCC GAC CCG
                             451                                             481
TCA CTG CCT ACG ACG GCT TCG TTC AGT ACA TTC CCT TTG ATG ATC CAC GGT TAC GAC ATT
                             511                                             541
TTA ACT AGC TCA GCC CCA GGG TTC TGT GAA GAC ATA AAG CTT GAC GAT AAA TCA TAT AAC
                             571                                             601
TCC AGT CCG TCA CTG CTC AAG AGC CGG CTC ATG GAG GAA TGC AGC CTG ATG GTG CCA TTT
                             631                                             661
GGA ATC CAC AGA GCT TAA TAC CCC CGT CGG GGG ATG AGA GAG GCC TGG TCT TGG CCG ATT
                             691                                             721
CCA GCC CCC GGT GGC TGT GGG GCC AGC CCC CCG GGG ATG GGG AAA ACA GTG GCC TCC CCA
                             751                                             781
ACC AGA GAG ACC GCT GTG TGG CAA GGG GAC AGT GGC CTG ATG TGA GAG GCA GCC AGC ACG
                             811                                             841
GGC ACA CTG GAA GAC AAG TTT CCT CCC CTT ACT CAC AGG GCG AGA GAC CTG CGA AAC TCA
                             871                                             901
AAC CAA GCT CAA AAA GTT CCA AAC TGG GAC TCG GAC CAA GAA AAG TTC AAA GAA AAA ATG
                                                                             MET
                             931                                             961
AAC GAG ACT ATA TTT TGC TTG GTT TCT ATC CCA GTG AAA TCA GAA TCA CAT CTG CCA GAT
ASN GLU THR ILE PHE CYS LEU VAL SER ILE PRO VAL LYS SER GLU SER HIS LEU PRO ASP
                             991                                            1021
AGA GAT ATG GAC AAC AAT GAC TTA AAG CCC AGT GCT GAT CAA AAG AAT GGG TCT GAT AAG
ARG ASP MET ASP ASN ASN ASP LEU LYS PRO SER ALA ASP GLN LYS ASN GLY SER ASP LYS
                            1051                                            1081
AGC CCG GCT CTG CAA GAA CAG AGT CTG CTG AGC ATG TCT TCC ACC GAC CTG GAG CTG CAG
SER PRO ALA LEU GLN GLU GLN SER LEU LEU SER MET SER SER THR ASP LEU GLU LEU.GLN
                            1111                                            1141
GCC CTC ACA GGA AGC ATG GGT GGG AGA ACG GAG TTC CAA AAA CAA GAT CTA GGG GAA CCA
ALA LEU THR GLY SER MET GLY GLY ARG THR GLU PHE GLN LYS GLN ASP LEU GLY GLU PRO
                            1171                                            1201
GAA GAA GAC AGA CAA ACA AAT GAC CTC AGT TTC ATC CAC CTT ACA AAG CAC AGA GAA CTC
GLU GLU ASP ARG GLN THR ASN ASP LEU SER PHE ILE HIS LEU THR LYS HIS ARG GLU LEU
                            1231                                            1261
AAG CAT TCT GGC TCT TGG CCA GGG CAC CGG TAC AGA GAT CAG CAA ACA CAA ACC AGT TTC
LYS HIS SER GLY SER TRP PRO GLY HIS ARG TYR ARG ASP GLN GLN THR GLN THR SER PHE
                            1291                                            1321
TCC GAG GAG CCC CAA AGT TCG CAG CTG CTC CCT GGT GCA AAG CTG GGA GGG CCG AGT CGT
SER GLU GLU PRO GLN SER SER GLN LEU LEU PRO GLY ALA LYS LEU GLY GLY PRO SER ARG
                            1351                                            1391
GCA GCA TTG AGT CCA AAA TGT TCA GAC CCT GCT GCC TCC GAA GCT CAG ACG CAC ACA GCG
ALA ALA LEU SER PRO LYS CYS SER ASP PRO ALA ALA SER GLU ALA GLN THR HIS THR ALA
```

FIG. 1(b)

```
            1411                                                              1441
TTC CCT ACC GGT GAT CAC AAA CAG AGG CCA AGT GCC CGT AAC CTG AAA GGT CAC AGG TCC
PHE PRO THR GLY ASP HIS LYS GLN ARG PRO SER ALA ARG ASN LEU LYS GLY HIS ARG SER
            1471                                                              1501
CTC AGC CCA TCC AGC AAC AGT GCG TTC TCA AGG ACT TCC TTG TCC GTG GAC CAG GCA CCG
LEU SER PRO SER SER ASN SER ALA PHE SER ARG THR SER LEU SER VAL ASP GLN ALA PRO
            1531                                                              1561
ACG CCA AAA GCA GGC CGA AGT CAG CCC TGC GTG GAT GTC CAC GGG CTT GGA GCC CAC CCT
THR PRO LYS ALA GLY ARG SER GLN PRO CYS VAL ASP VAL HIS GLY LEU GLY ALA HIS PRO
            1591                                                              1621
GGG CCT AAG CGG GAG GTG GTG AAG GGG GAG CCC ACG GGC CCT TGC AAC AGT AAA CAA CTC
GLY PRO LYS ARG GLU VAL VAL LYS GLY GLU PRO THR GLY PRO CYS ASN SER LYS GLN LEU
            1651                                                              1681
TTT GGG CAG TTT CTC CTG AAA CCG GTC AGC CGT CGT CCC TGG GAT TTG ATC AGT CAG TTA
PHE GLY GLN PHE LEU LEU LYS PRO VAL SER ARG ARG PRO TRP ASP LEU ILE SER GLN LEU
            1711                                                              1741
GAA AGT TTT AAC AAG GAG CTC CAG GAA GAG GAA GAA AGC AGC AGT AGC AGC AGC AGC AGC
GLU SER PHE ASN LYS GLU LEU GLN GLU GLU GLU GLU SER SER SER SER SER SER SER SER
            1771                                                              1801
AGC AGC AGC AGT GAG GAG AGT GAG GCG GAG CCG CAG CAG GAG AAC CGT GCT CAC TGC AGA
SER SER SER SER GLU GLU SER GLU ALA GLU PRO GLN GLN GLU ASN ARG ALA HIS CYS ARG
            1831                                                              1861
CAG GAG GAT GTG GGC TTC CGC GGA AAC AGC CCG GAA ATG AGG GTT GAG CCA CAG CCG AGG
GLN GLU ASP VAL GLY PHE ARG GLY ASN SER PRO GLU MET ARG VAL GLU PRO GLN PRO ARG
            1891                                                              1921
ATG TGG GTG CCG GAG AGC CCT GTG TGT AGG TCG GGA AGA GGT GAG AGT AAG TCT GAG AGC
MET TRP VAL PRO GLU SER PRO VAL CYS ARG SER GLY ARG GLY GLU SER LYS SER GLU SER
            1951                                                              1981
TGG AGT GAG GAG CTG CAG CCT GGC CAC CCA CGT GCC TGG CCT CCA TCC CCG GGC CGC TTT
TRP SER GLU GLU LEU GLN PRO GLY HIS PRO ARG ALA TRP PRO PRO SER PRO GLY ARG PHE
            2011                                                              2041
CGC GTG GAA GAA GGT GGC GGT GCA CCT TTC TGC TCA GCA GAT GGA AGC ACG AGT GCA GAG
ARG VAL GLU GLU GLY GLY GLY ALA PRO PHE CYS SER ALA ASP GLY SER THR SER ALA GLU
            2071                                                              2101
AAG GGA CAC CTG GAG GTT AGC AAC GGA ATG GAC GAG CTG GCA GGT AGC CCA TTT CCT GTG
LYS GLY HIS LEU GLU VAL SER ASN GLY MET ASP GLU LEU ALA GLY SER PRO PHE PRO VAL
            2131                                                              2161
ACG AGA ATG TCT TCA AGA TCA AGT GAC GCA AAA CCA CTG CCC GCG TCC TAT CCA GCT GAA
THR ARG MET SER SER ARG SER SER ASP ALA LYS PRO LEU PRO ALA SER TYR PRO ALA GLU
            2191                                                              2221
CCT AGG GAG CCC CAG GAA AGT CCG AAA ATC ACC AGT GCT TTC AGC TCT GTG AAA CCA AGT
PRO ARG GLU PRO GLN GLU SER PRO LYS ILE THR SER ALA PHE SER SER VAL LYS PRO SER
            2251                                                              2281
GAA GCG GTC CCT CGG AAG TTT GAC AGT GGT GGA GAG AGG GGG GCA GGG CTC CCA CTG TCC
GLU ALA VAL PRO ARG LYS PHE ASP SER GLY GLY GLU ARG GLY ALA GLY LEU PRO LEU SER
            2311                                                              2341
CTG TCT AAC AAG AAC CGA GGG CTC TCA GCT CCA GAC TTA CGG TCT GTG GGG CTC ACC CCT
LEU SER ASN LYS ASN ARG GLY LEU SER ALA PRO ASP LEU ARG SER VAL GLY LEU THR PRO
            2371                                                              2401
GGG CAA GAA CAG GGT GCC AGT GAG CTA GAG GGG TCT TTG GGT GAA GCA AGC ACA ATA GAA
GLY GLN GLU GLN GLY ALA SER GLU LEU GLU GLY SER LEU GLY GLU ALA SER THR ILE GLU
            2431                                                              2461
ATC CCC CCA GGT GAG TCC TTG CAA GCC AGG GCT GCA AGG ATC CTG GGC ATT GAG GTG GCG
ILE PRO PRO GLY GLU SER LEU GLN ALA ARG ALA ALA ARG ILE LEU GLY ILE GLU VAL ALA
            2491                                                              2521
GTG GAG TCC CTC CTG CCG GGC ATC CGG AGA GCG GGA CAG AAC CAG CCT GCT GAG CCC GAT
VAL GLU SER LEU LEU PRO GLY ILE ARG ARG ALA GLY GLN ASN GLN PRO ALA GLU PRO ASP
```

FIG. 1(c)

```
                2551                                              2581
     GCA AGT GCC TGC ACC CCA GAG TCC CCC CAG GAA GAG TTG CTA TCT CGC CCA GCA CCG GCA
     ALA SER ALA CYS THR PRO GLU SER PRO GLN GLU GLU LEU LEU SER ARG PRO ALA PRO ALA
                2611                                              2641
     GAT GTC CCC AGG GTG TCC ACT GAT GCC TTT TAT GGC AGG AGG AAG TGC GGC TGG ACC AAG
     ASP VAL PRO ARG VAL SER THR ASP ALA PHE TYR GLY ARG ARG LYS CYS GLY TRP THR LYS
                2671                                              2701
     AGC CCT CTC TTT GTA GGG GAC AGG GAC AGT GCC AGG CGG GCT CCT CAG GCT TTT GAG CAC
     SER PRO LEU PHE VAL GLY ASP ARG ASP SER ALA ARG ARG ALA PRO GLN ALA PHE GLU HIS
                2731                                              2761
     TCA GAT GTG GAC GGG GTT GTC ACC AGC ACA GAC CCT GTC CCT GAG CCT GAG CCC AGC CCC
     SER ASP VAL ASP GLY VAL VAL THR SER THR ASP PRO VAL PRO GLU PRO GLU PRO SER PRO
                2791                                              2821
     TTT GAG TCC AAG TTC TTC GAA CAA AAG GAT GTG GAA ACA AAA CCA CCC TTC AGG TCC ACT
     PHE GLU SER LYS PHE PHE GLU GLN LYS ASP VAL GLU THR LYS PRO PRO PHE ARG SER THR
                2851                                              2881
     TTA TTC CAT TTT GTA GAA AGA ACC CCA AGT GTG GCA GGC TCT GAA AAG AGA CTT AGA AGC
     LEU PHE HIS PHE VAL GLU ARG THR PRO SER VAL ALA GLY SER GLU LYS ARG LEU ARG SER
                2911                                              2941
     CCT TCC AAA GTG ATT GAA AGT TTA CAA GAG AAA CTG GCC TCC CCG CCT AGG AGA GCA GAC
     PRO SER LYS VAL ILE GLU SER LEU GLN GLU LYS LEU ALA SER PRO PRO ARG ARG ALA ASP
                2971                                              3001
     CCT GAC CGC CTG ATG AGA ATG AAA GAG GTG AGC TCA GTG TCA CGG ATG AGA GTC CTG AGC
     PRO ASP ARG LEU MET ARG MET LYS GLU VAL SER SER VAL SER ARG MET ARG VAL LEU SER
                3031                                              3061
     TTC AGG AAT GCC GAC TCC CAG GAG GAC GCC GAG GAA TTG AAG GCC ACC ACA AGG GGC CAG
     PHE ARG ASN ALA ASP SER GLN GLU ASP ALA GLU GLU LEU LYS ALA THR THR ARG GLY GLN
                3091                                              3121
     GCC GGG CTC CCG GGA GGC CTT GTG TCT CCT GGC AGT GGG GAC CGT GCC CAG AGA TTG GGC
     ALA GLY LEU PRO GLY GLY LEU VAL SER PRO GLY SER GLY ASP ARG ALA GLN ARG LEU GLY
                3151                                              3181
     CAC TCA CTC TCT GTG TCC AAG GAC AGC ATC TCC AGG GAA GAG AAG GAG CAT CCG GCA GCA
     HIS SER LEU SER VAL SER LYS ASP SER ILE SER ARG GLU GLU LYS GLU HIS PRO ALA ALA
                3211                                              3241
     CAA AAG GAG AAG AGC ATG GAT CAA GAC TTC TGG TGC CCA GAT TCC TAT GAC CCT AGC AGA
     GLN LYS GLU LYS SER MET ASP GLN ASP PHE TRP CYS PRO ASP SER TYR ASP PRO SER ARG
                3271                                              3301
     GTG GAG AGG GTG TGA TGA AAT GTC GGT GGA GCT TGC ATT CCG TTG CGA ATT GAG TAT TCT
     VAL GLU ARG VAL END END
                3331                                              3361
     CAA GTA GCT GGT AGA TTT AGT CTA TCA GCC CCA CTT CCC CAT GTA GAA GCT GGA AGC TGC
                3391                                              3421
     TGA GTT TTT AGC ATC CTG ATA ACA TTC TTT ACC ACT GCC ACT AGG AAA CTT GCC ATC CTC
                3451                                              3481
     TCA GAA TTG CTT TGT GGC GAT AAA GCA ATC GTC CGT TGA AAC CAT CTG TTT TTA TAG CAT
                3511                                              3541
     GCA AGA TTT AAT GCC TAT AAT TAG GAA GGA GTT TTC ACA GAA ACC CTC CCT CAT GAC AGA
                3571                                              3601
     TTT GAC TAA GCT GGT AAA TAG TTT GGT GTT GCT CTC ATT CTG GGT GAA GAT TTC AAT GTG
                3631                                              3661
     GAA GAT CTA GCA AAT GCT TTG GAA ACC GGC CTG TGA ATG GTG TGC TCC CTC TGT GTC TCC
                3691                                              3721
     ATG GCC TGC AGT CCA TGC TCC TTG TGA AGG AGT TTG GGA CAC TGG CTG TTG CCC GGT GTT
                3751                                              3781
     TCA GCA CTT TCA GTT TAG GGG AAA TGT GAA TCA ATA GGT ATG ATC CAT TTC TAA TCA ATT
                3811                                              3841
     TGG CCT TCT GCT GCT GGA AGT AAC TTT ACT TAT AAG TAA CTT GCC ATC AGA GAA TAA AAG
                3871
     CAA TAT CTT TTA AGT TCC TGA AAA ATT AAA AAA AAA AAA ACC CGA ATT
```

FIG. 2(a)

PROTOCOL FOR CLONING Hu-TYPE I IFN RECEPTOR

1. CO-TRANSFECTION AND HAT SELECTION

TOTAL HUMAN DNA FROM T CELL LEUKEMIA
MOLT 4 CELLS PLUS pAGO HSV TK+

MOUSE LM TK- CELLS → SELECTION IN HAT MEDIUM → TRANSFECTANTS

2. FACS SELECTION OF CELLS EXPRESSING IFN RECEPTOR

Hu-IFN-$\beta_1$ 200 U/ml
ANTI-H-2K$^k$
10% MOST FLUORESCENT
CELL NUMBER vs FLUORESCENCE
10%

3. TESTING OF CELLS FOR RESPONSE TO HU-IFN-$\alpha$ or -$\beta$

CLONE → TREAT WITH Hu-IFN TEST RESPONSE → (2'-5') A SYNTHETASE
ANTIVIRAL STATE
MHC INDUCTION

4. RETRANSFORM WITH DNA FROM POSITIVE CLONE
   RESELECT FOR TK+ CELLS
   RESORT FOR MOST FLUORESCENT CELLS
   SUBCLONE
   TEST FOR RESPONSE TO HUMAN TYPE I IFN'S

FIG. 2(b)

5. PREPARATION OF GENOMIC LIBRARY IN EMBL - 3λ VECTOR

SCREEN WITH TOTAL HUMAN DNA
   PURIFY PHAGES CONTAINING HUMAN REPETITIVE DNA

6. RESTRICT EMBL-3λ PHAGES, RE-SCREEN FOR UNIQUE DNA SEQUENCES AND SUBCLONE THEM INTO pGEM-4

7. DETERMINE CHROMOSOMAL ORIGIN OF UNIQUE SEQUENCES.

SELECT THOSE FROM HUMAN CHROMOSOME 21.

8. SCREEN a HUMAN PLACENTA λgt II cDNA LIBRARY WITH UNIQUE CHROMOSOME 21 PROBE.

9. SUBCLONE cDNA FROM λgt II INTO BLUESCRIPT VECTOR

TRANSCRIBE / TRANSLATE
   SEQUENCE

10. SUBCLONE cDNA INTO EUCARYOTIC EXPRESSION VECTOR pSVE3

CHARACTERIZE:
    1. TRANSIENT TRANSFECTION OF CELL LINES
    2. STABLE TRANSFECTIONS

FIG. 3

L-7 RESTRICTION MAP UNIQUE SITES (3896 BP)

OLIGO PEPTIDE

PN2

PSN

DNA CLONING AND EXPRESSION OF AN L7 PROTEIN WHICH MODULATES THE 2'-5' OLIGOSYNTHETASE AND H2-K*K RESPONSE TO TYPE-I INTERFERON

This application is a continuation of application Ser. No. 07/436,332, filed Nov. 14, 1989 now abandoned.

BACKGROUND OF INVENTION

1. Field of Invention

The present invention relates to the molecular cloning of a gene encoding a polypeptide which modulates cellular response to type I interferon, such polypeptide being a putative component of the interferon type I receptor system, and expression of the gene in a suitable host. The present invention relates to the polypeptide itself, active analogs thereof and processes for obtaining polypeptides with such properties.

2. Information Disclosure Statement

Human and murine cells can be induced to make three classes of interferon (IFN) designated alpha, beta, and gamma on their basis of their antigenic properties and on the type of cell producing them. These IFN's in turn induce a number of changes in human cells which result in establishment of an antiviral, anti-tumor, and/or anticellular state, and cause a number of alterations in the cell membrane including induction and/or increased expression of major histocompatibility complex (MHC) antigens. Lindhal, P. et al (1973), "Enhancement by interferon of the expression of surface antigens on murine leukemia L 1210 cells," *Proc. Natl. Acad. Sci.(USA)*, 70, pp 2785-2788; and Fellous, M. et al (1982), "Interferon-dependent induction of mRNA for the major histocompatibility antigens in human fibroblast and lymphoblastoid cells," *Proc. Natl. Acad. Sci.-(USA)*, 79, pp. 3082-3086. Most, or all, of these changes are triggered by the signal generated by interaction of IFN's and their cell surface receptors.

Direct ligand binding studies and binding site competition studies as well as indirect immunological and somatic cell genetic studies demonstrate that the three classes of IFN's interact with interferon sensitive cells through specific binding to one of two types of high affinity receptors on the cell surface (reviewed in Rubinstein, M. and Orchansky, P. (1985), "The Interferon Receptors, "*CRC Critical Reviews in Biochemistry*, 2 p. 249). All human IFN-alpha's and human IFN-$\beta$ (Type I IFN's) bind to a chromosome 21-encoded Type I receptor, while human IFN-gamma (Type II IFN) binds to a chromosome 6-encoded Type II receptor which requires a chromosome 21-encoded gene product in order to confer sensitivity. The IFN receptor required for MHC induction and the IFN receptor which triggers antiviral state (AVS) induction share common antigenic determinants and are encoded on human chromosome 21.

The human type I IFN receptor has been estimated to have a molecular weight of 95-140 kDa, based on experiments in which cell membrane having bound $^{125}$I-IFN are cross-linked and run on SDS-PAGE (Razziudin, A. et al. (1984), *Proc. Natl. Acad. Sci.(USA)*, 81 pp. 5504-5508 and Thompson, M. R. et al. (1985), J,. Biol, Chem., 260, pp. 563-571). There is some evidence that the receptor is a glycoprotein and the lower values may be closer to the size of the polypeptide itself.

No admission is made that any reference cited herein qualifies as pertinent prior art. All publications cited herein are hereby incorporated by reference.

SUMMARY OF THE INVENTION

Despite the considerable interest in the interferon system, and the cloning of the alpha and beta interferon genes several years ago, the Type I receptor has neither been isolated from nature and purified, nor produced by recombinant DNA techniques.

It has not been possible to isolate IFN-$\alpha,\beta$ receptors by direct protein purification because of their scarcity (a few thousand molecules per cell) and of the absence of cell lines with an amplified number of receptors. To overcome this difficulty, the present inventors approached the problem by DNA-mediated gene transfer. By transforming mouse cells with human genomic DNA and selecting cell clones which have acquired increased ability to respond to human alpha and beta IFN, the gene for a protein component of the Type I IFN receptor system was successfully isolated. The present inventors chose to use the increase in H2 antigens of the cell surface as a means to isolate human IFN responder cells.

The present invention relates to a DNA sequence comprising the DNA sequence encoding a protein which modulates cellular response to Type I interferon and is thus a putative component of the human interferon Type I receptor system. In a preferred embodiment, it relates to the cDNA of FIG. 1 comprising the coding region 899-3253.

The present invention also relates to a DNA vector including the DNA of the invention, and preferably to an expression vector consisting essentially of the plasmid pSVE3-L7 containing the cDNA of FIG. 1 fused to the Simian Virus (SV) 40 early gene promoter.

It further relates to host cells, preferably eukaryotic, e.g. mammalian cells, transformed with a DNA of the invention in a manner allowing the host cell to express said human IFN type I receptor-related poly-peptide, and to the polypeptide thus expressed.

BRIEF DESCRIPTION OF THE DRAWINGS

FIG. 1 is the nucleotide sequence of the putative Type I interferon receptor component cDNA clone L7. The coding sequence is identified and the predicted translation into amino acids is given.

FIG. 5A is a graph plotting (2'-5') A synthetase activity in CHO-pSVL7 transformants (at 300 nM MTX)

against the activity in CHO-DHFR controls for cells induced by either human IFN-β (squares) or hamster IFN (crosses).

DETAILED DESCRIPTION OF THE INVENTION

Receptors for cytokines or other protein hormones are protein molecules on the surface of cells which interact with specificity with a ligand (i.e., the cytokine or hormone) present in the extracellular environment and transfer a signal into the intracellular compartment in order to effectuate the biological action of the ligand. Known receptors for cytokines (e.g., interleukin-2 (IL-2), interferon-γ (IFN-γ)) are composed of several different protein chains which together compose the receptor system. The function of these protein chains are 1) to bind the ligand specifically at high affinity, 2) to interact with the active site of the ligand which often produces a conformational change, and 3) to transduce a signal into the intracellular compartment. Cooperation between the different proteins forming the receptor system is considered to be a requirement for these functions. For example, high affinity binding of IL-2 requires two components (Hatakeyama M., et al (1989), "Interleukin-2 receptor β chain gene: Generation of three receptor forms by cloned human α and β chain cDNAs",*Science*, 244,551–556). The type II interferon receptor system is composed of at least two components: a binding unit and a transducing unit (Langer J. A. and Pestka S., (1988) "Interferon receptors", *Immunology Today*, 9, 393–400). It is likely that the type I IFN receptor system is similarly composed of several proteins involved in species-specific binding of IFN, interaction with IFN active site and transduction of the signal which activates transcription of specific genes.

While it is known in the art to cross-link an interferon to its cell surface receptor, this method cannot practically be used to identify transformed cells bearing the Type I receptor or to obtain sufficient receptor to purify and characterize it, since the number of receptors per cell is low (typically, less than 5,000). Moreover, this method would not have identified the L7 protein since it does not appear to bind IFN at high affinity.

In one aspect, the present invention relates to a method of identifying a gene encoding a receptor component for a cytokine, particularly an interferon, and more especially a Type I interferon, which avoids the need to attempt to cross-link a labeled cytokine to a surface receptor expressed by the transformed cells and then, through detection of the bound label, distinguish cells expressing such a receptor from those which do not. Instead, the present invention relies on the ability of the cytokine to induce a detectable change in a cell surface characteristic. In a preferred embodiment, this change is an antigenic change. The change may be an increase or a decrease in one or more antigens. By way of example, with interferon one such change is an increase in MHC antigens; it is preferred to detect the increased expression of the H2 antigen, but other MHC antigens may similarly be detected, as, for example, β2 microglobulin or class II MHC antigens.

This procedure has several advantages over the method discussed above. First, it is capable of identifying cytoplasmic receptors, not merely cell surface receptors. Second, it is capable of identifying receptors which interact only indirectly with the corresponding ligand, not merely those which bind the ligand directly. Finally, it ensures that the selected clones are competent to respond to the ligand. The simplistic method can select clones expressing a molecule which binds interferon but does not, as a result of that interaction, trigger any further cellular activity.

Preferably, the cell surface antigen is recognized by an antibody, especially a monoclonal antibody. However, in certain cases, a different class of binding molecule, such as a lectin or an enzyme, may be suitable. In one embodiment, the binding molecule must be labeled. Any label known in the assay art, such as a radiolabel, enzyme label or fluorescent label, may be employed; the fluorescent label is preferred. The label may be attached directly or indirectly, covalently or noncovalently. Alternatively, the binding molecule may be attached to an affinity chromatography support and cells bearing the receptor can then be affinity separated from those which do not.

Separation of the desired clones from the other transformed cells is preferably accomplished by fluorescence-activated cell sorting (FACS). The level of expression of the detected surface structure must of course be within the sensitivity limits of FACS, typically over 20,000 molecules/cell.

The receptor component gene must be isolated from DNA containing unrelated genes as well as sequences without coding function. The DNA to be screened may be genomic DNA or cDNA. It may be derived from the entire genome of the donor, or from a selected chromosome. It may be enriched for DNA of a particular size. The DNA may be introduced into the host cell by simple transfection of DNA fragments, or the DNA fragments may be subcloned into a suitable viral or plasmid vector which is then used to transform the host cell.

The host cell used for screening is preferably one which, prior to transformation with a functional receptor gene, is incapable of responding to the interferon (or other cytokine of interest). However, a host cell with a low level of response can be used if the genetic modification substantially enhances the response to be detected. Since interferons are species-specific, in searching for the human IFN receptor component gens, the use of a non-human host cell is preferred.

Once the receptor component gens has been isolated, non-naturally occurring analoguss of the receptor component are readily prepared by site-specific mutagenesis of the gens, or by chemical treatment (e.g., with proteolytic enzymes). Analoguss likely to be functional can be identified by careful study of the sequence. For example, potential phosphorylation and transmembrane regions are more likely to be essential to activity. It is better to replace an amino acid with one of similar size and charge than with a radically different amino acid. The N- and C-termini may be truncated to determine which is necessary for activity.

The receptor component gene may be linked to a non-natively associated promoter, which may be constitutire or inducible. The preferred promoter is the SV40 early promoter. The codon selection of the gens may be modified to match the codon preferences of the host, to eliminate undesirable secondary structure formation, or to facilitate further modifications of the gens by creating or eliminating restriction sites. The gens may be introduced into any suitable host cell.

In an especially preferred embodiment, sheared human DNA was introduced into mouse LTK− cells together with a Herpes virus TK gens and LTK+ transfected mouse cells which respond to human type I IFN's were selected by fluorescence activated cell sorting (FACS). Indirect, rather than direct, FACS selection for receptor component was used because the number of Type I IFN receptors/cell is below that which can be detected by FACS analysis. The IFN induced increase in MHC antigens on the cell surface was chosen for use as a marker to separate responder cells.

Specifically, cells expressing biologically active receptor components, as evidenced by increased H2 expression after treatment of HAT resistant cells with human Type I IFN, were screened for. This is an approach supported by demonstration that human IFN regulates mouse H2 expression in human x mouse somatic cell hybrids expressing human IFN receptors. Cells were cultured and the FACS selection repeated. The amount of human DNA in the mouse cells was decreased by making a secondary transfection using DNA from human IFN sensitive cloned cells from the primary transfections. Secondary transfectants expressing the receptor component were obtained by FACS screening as described above.

Genomic DNA libraries were prepared from DNA extracted from the secondary transfectants using bacteriophage EMBL3. Human DNA restriction enzyme fragments from these phages were analyzed by Southern blot analysis to obtain unique sequences expressed in cells containing human chromosome 21. One phage isolate contained a unique 2.1 kb EcoR1 restriction fragment which appeared to be from human chromosome 21 on the basis of differential hybridization to genomic DNA from mouse cells vs. human placental DNA and DNA from a human x mouse somatic cell line in which human chromosome 21 was the only human chromosome retained. It was confirmed that this was indeed a piece of human chromosome 21 by its hybridization pattern on pulse field gel blots using DNA from human x mouse and human x hamster somatic cell hybrids with and without human chromosome 21. It has been shown using Northern blot hybridization that this unique fragment hybridizes with human poly-A+ RNA large enough to encode the receptor component. This piece was subcloned into plasmid vector pGEM 4 and used to screen a human placenta λgt11 cDNA library purchased from Clonetech Laboratories (Palo Alto, Calif.). Seven cDNA clones were isolated. The human DNA has been subcloned into the Bluescript plasmid vector of Stratagene Cloning Systems (San Diego, Calif.).

EXAMPLE 1

Isolation of the Putative Type I IFN Receptor Component Gene

Mouse LM TK cells (lacking the enzyme thymidylate kinass, TK) were transfected by total human DNA from the T cell leukemia Molt-4 cells using a plasmid pAGO harboring the Herpes Simplex Virus TK− cDNA as the selectable marker in Hypoxanthine-Aminopterin-Thymidine (HAT) selective medium. LM TK+ cells were exposed to 200 U/ml human IFN-β1 and stained with monoclonal antibody anti-H2K$^k$ 12–41 (see Rosa, et al. (1986), *Interferon*, 7, 47–87, Academic Press, incorporated by reference) and FITC-(Fab') rabbit antimouse IgG. Using a cytofluorograph 50HH (Orthodiagnostics), the 10% most fluorescent cells were sterilely sorted, regrown and subjected to a second round of selection. Preliminary experiments established that the twice sorted population was enriched in cells responding to human IFN-alpha or beta (but not gamma) in multiple tests such as induction of the (2'-5') oligo A synthetase, resistance to Vesicular Stomatitis Virus, and $^{125}$I-IFN-alpha binding. Clones with this phenotype were derived by dilution.

Polyclonal and monoclonal antibodies to mouse-human hybrids containing only human chromosome 21, which inhibit the binding and response to human (but not mouse) IFN (see Razziudin et al., cited above), blocked the H2 increase by human IFN in the positive clones indicating the presence of the human IFN surface receptor. DNA of one such primary transformant was transfected into new LM TK−cells and secondary transformants were obtained using pAGO for selection. Secondary transformants were again subjected to FACS selection as above and after three cycles, clones were derived by dilution and human IFN responders identified by the tests described above. DNA was prepared from subclone cultures which were simultaneously tested for (2'-5') oligo A synthetase induction by human IFN. Subcloning or repeated FACS selection was found to be needed to maintain consistent levels of the phenotypic response. One clone, named βII-19-26 was selected for further analysis.

Southern blot analysis with a total human DNA probe showed that the content of human DNA in some of the clones was low enough to warrant attempts at molecular cloning of the transforming DNA. A genomic library was prepared from clone βII-19-26 using the EMBL-3 vector, and screened with total human DNA as probe. About 20 EMBL-3 phages containing human repetitive DNA were purified. From two of the phages giving the strongest signal (15-4 and 6-40), BamHI restriction fragments of 2.1 and 1 kb containing no repetitive DNA were isolated. Southern blot analysis of genomic DNA confirmed that these fragments hybridized with human but not mouse DNA. The majority of phages with human DNA from the βII-19-26 library hybridized with the BamHI 2.1 kb fragment (probe 6-40-3) indicating that this is a major constituent of the human DNA in the βII-19-26 cells. The chromosomal origin of the 6-40-3 probe was determined by hybridization to Southern DNA blots from mouse-human and hamster-human hybrids, which confirmed that the 6-40-3 probe identifies a 300 kb NotI fragment originating from chromosome 21. The 6-40-3 BamHI fragment of 2.1 kb overlaps two EcoRI fragments of 2 and 4 kb, the total length of the insert in phage 6-40 being 16 kb. DNA from transformant subclones which either respond to human IFN or lack the phenotype were probed with 6-40-3; only responders showed specific hybridization to the probe.

To determine whether the 6-40-3 probe was part of a transcription unit, we screened a lambda gtll cDNA library from human placenta with this probe. Seven positive cDNA clones were identified in the $2 \times 10^6$ phages. One clone (L7) has an EcoRI insert of 3.9 kb indicating a long transcription unit. This was confirmed on Northern blots where the same probe detected a 4.5 kb RNA, and a larger 5.1 kb band. The EcoRI insert of cDNA clone L7 of 3.9 kb was subcloned in a Bluescript vector (Stratagen Co.) and E. coli TCl competent bacteria were transformed with this LT-BS2 vector. This transformed bacteria was deposited with the Collection Nationals de Cultures de Microorganismes (C.N.C.M.), Paris, France, on November 14, 1988, under the accession number C.N.C.M. 1-816, in accordance with the Budapest Treaty. Subcultures will be made available to the public as required by the Treaty, but no license can be inferred from the deposit.

The subcloning was carried out in two orientations. T7 RNA polymerass transcripts translated in reticulocyte lysates produced a 100 kd protein in one orientation but not the other. A 62 kD protein was made by the same transcripts producing the 100 kD protein, and may be translated from an internal ATG codon.

EXAMPLE 2

Characterization of the Cloned Putative IFN Type I Receptor Component

The nucleotide sequence of the L7 cDNA was established by sequencing nested deletions from both strands in the Bluescript vector. The sequence shown in FIG. 1 indicates an RNA of 3870 nucleotides followed by a poly A tail. An open reading frame starts at nucleotide 899 and ends at 3253 encoding a protein of 785 amino acids. The location of the coding region 899–3253 was confirmed by translation of deletion transcripts in reticulocyte lysates.

The length of the protein predicts a molecular weight of 86,000 which is close to the lower values calculated by gel electrophoresis. From the electrophoresis of the translation product of the L7 cDNA in reticulocyte lysate, it appears that the protein migrates more slowly than theoretically expected, with an apparent molecular weight of 100,000. This can be explained by the abundance of acidic amino acids in the sequence.

An interesting feature of the L7 protein is a region of 12 contiguous serines flanked by 6 glutamic acids (bases 1710–1760 in FIG. 1). This region could be phosphorylated. A potential transmembrane region with 15 uncharged amino acids is present from nucleotides 3056 to 3100 in FIG. 1. A hydrophobic signal peptide is observed at the N-terminus of the protein. These features are in line with the location of this protein in the cell membrane as expected for the IFN type I receptor. There is no significant homology between the L7 protein sequence and the IFN-$\gamma$ receptor or any other known gens.

Since final proof of identity requires demonstration of acquired sensitivity to human IFN in non-human cells transfected with this eDNA clone, transient and stable transfections of the eDNA gens fused to the SV40 early promoter were analyzed in various non-human cell lines.

To test the biological activity of the protein encoded by the L7 cDNA, an expression vector pSVE3-L7 was constructed containing the entire L7 cDNA fused to the Simian Virus 40 early gens promoter. For transient expression this plasmid was transfected into mouse cells and 24 hours later the cells were treated by 500 U/ml human IFN-$\beta$1 or left untreated (Benech, P., et al. (1987), Mol. Cell. Biol., 7 pp. 4498–4504). After another 24 hours Cell extracts were prepared and (2'–5') oligo A synthetase was measured as described (Revel M. et. al. (1981), Meth. Enzymol, 79, p. 143). The (2'–5') oligo A synthetase activity in transfected cells treated by human IFN minus that in non-treated cells was calculated. As shown in Table 1, this increase was on the average 4.5 fold higher in the cells which had received the expression vector containing the L7 cDNA versus the cells which had received the empty expression vector. The latter showed no significant increase over cells which had received no DNA at all (Table 1).

Figure 4:
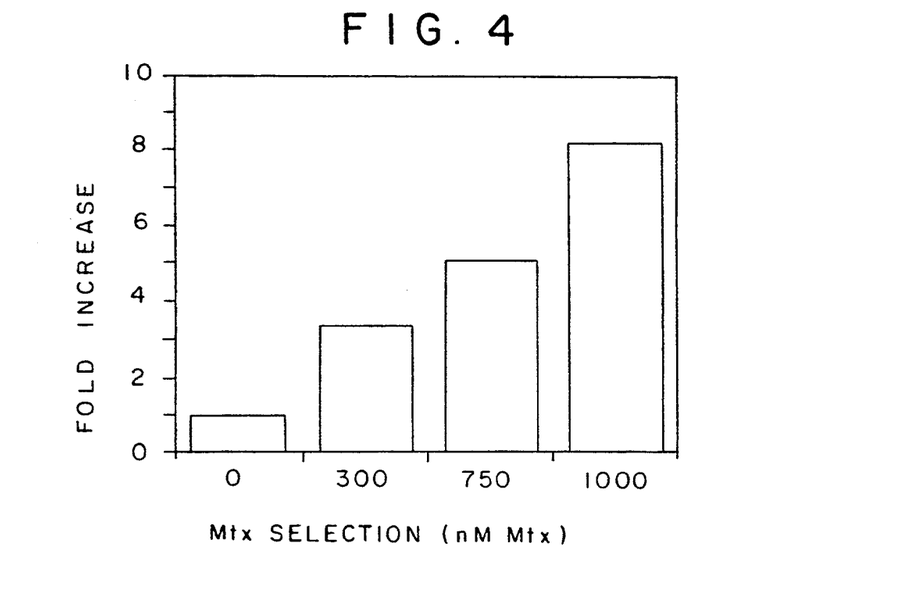
FIG. 4 is a bar chart showing the amplification of the L7 cDNA expression in CHO cells by methotrexate (MTX) expressed as the response of cells to human IFN, (i.e., fold increase of (2'-5') A synthetase). The fold increase for CHO-pSVL7 clones selected with each MTX concentration was calculated by comparison to control CHO-DHFR clones subjected to same treatment. The (2'-5') A synthetase increase in non-amplified clones (0 MTX) was two-fold over CHO-DHFR, and in the ordinate, this value is taken as 1 for comparison to the amplified clones.

Stable transformants of Chinese Hamster Ovary cells (CHO) were prepared by cotransfection of the cDNA fused to the SV40 early promoter and vectors containing the DHFR gens. Clonal cell populations were isolated from transfection after appropriate selection and these clonal lines were screened for the presence of the cDNA and for response to human IFN-$\beta$ as shown by induction of (2'–5') A synthetase. Clones containing L7 DNA by Southern Blot analysis and responding to 100 U/ml human IFN-$\beta$1 by (2'–5')-A synthetase induction higher than CHO-DHFR+ cells, were isolated and subjected to amplification by stepwise selection with methotrexate (MTX). In clones resistant to 50 nM or, better, 300 nMMTX, L7 RNA expression becomes detectable by Northern blots of total RNA. The response to 100 U/ml human IFN-$\beta$1 is 4–5 fold higher in the 50 nM MTX clones than in CHO cells containing pSVDHFR only, which were similarly amplified (Table 2). At 300, 750 and 1000 nM MTX, the CHO-DHFR+L7 clones showed an increase in the response to human IFN-$\beta$ as compared to the highest response in CHO-DHFR control clones which were similarly treated by MTX (FIG. 4). The amplitude of the response to human IFN-$\beta$ increases, therefore, with gene amplification by a factor of 8 fold. The response of such amplified clones to 100 U/ml human IFN was about 15% of that to 20 U/ml hamster IFN.

The present inventors have concluded that, although expression of the L7 cDNA under SV40 promoter control leads to increased response of the cells to human IFN, the amplitude of the response remains low. This may be due either to problems in expression of the protein or to the fact that the L7 protein is only one part of the IFN receptor system. The latter possibility seems more likely as significant high affinity binding of human $^{125}$I-IFN-$\alpha$ to the CHO transformants was not able to be demonstrated. If the receptor is composed of more than one chain, binding affinity may be very low in the presence of only one of the protein chains.

Figure 5A:
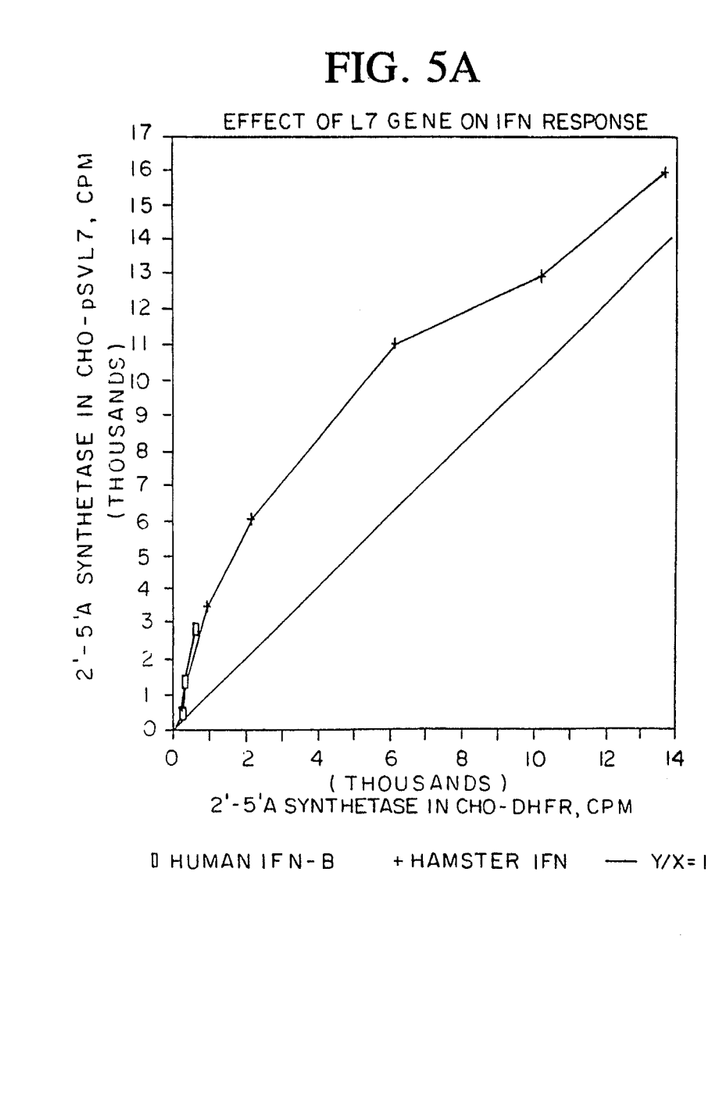
Figure 5B:
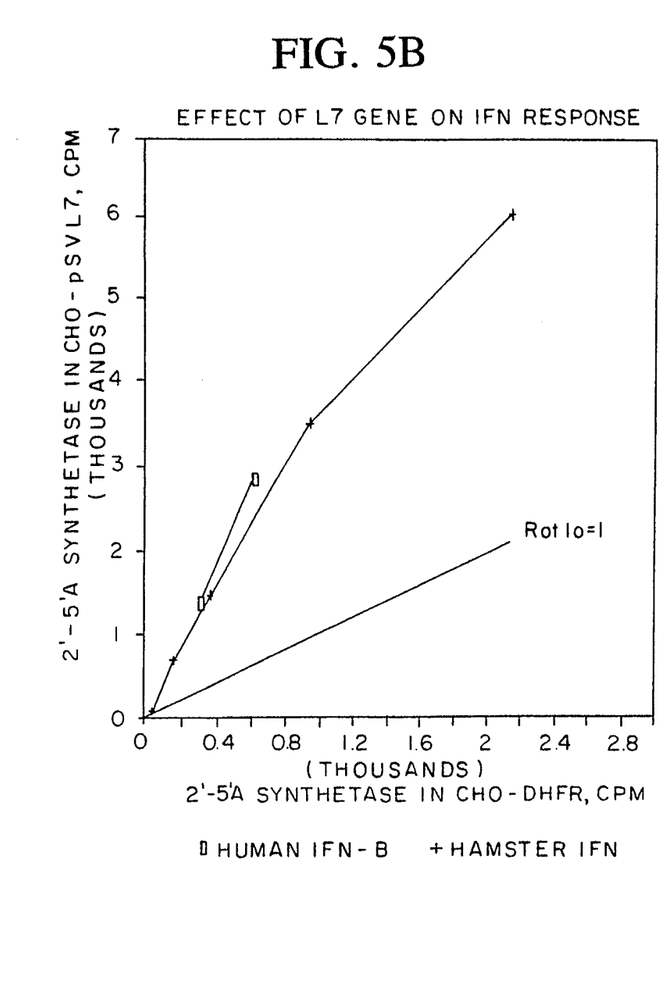
FIG. 5B shows an expanded plot of the data in FIG. 5A.

That the L7 protein is a component of the IFN receptor which is not directly responsible for the species specific binding of human IFN is further shown by the fact that in the amplified CHO-pSVL7 clones, the response to hamster IFN is also increased. FIG. 5 shows that at low concentration of hamster or human IFN, which produce low stimulation of (2'–5') A synthetase activity in the control CHO-DHFR clone (abscissa), a CHO-pSVL7 clone (300 nM MTX) gave a 5 fold higher response with either of the two IFN species (the straight line in FIG. 5 is the expected line if both clones respond equally). At higher IFN concentrations producing higher induction of (2'-5') A synthetase, the difference between the CHO-pSVL7 and CHO-DHFR clone was less marked. The present inventors have concluded that having more L7 protein on the surface allows the cells to respond better to low concentrations of IFN. This result is in agreement with the hypothesis that L7 is one of the chains of the type I IFN receptor system, which acts in transducing the signal within the cell.

EXAMPLE 3

Antibodies to L7 protein show the protein on the surface of cells

Figure 2A:
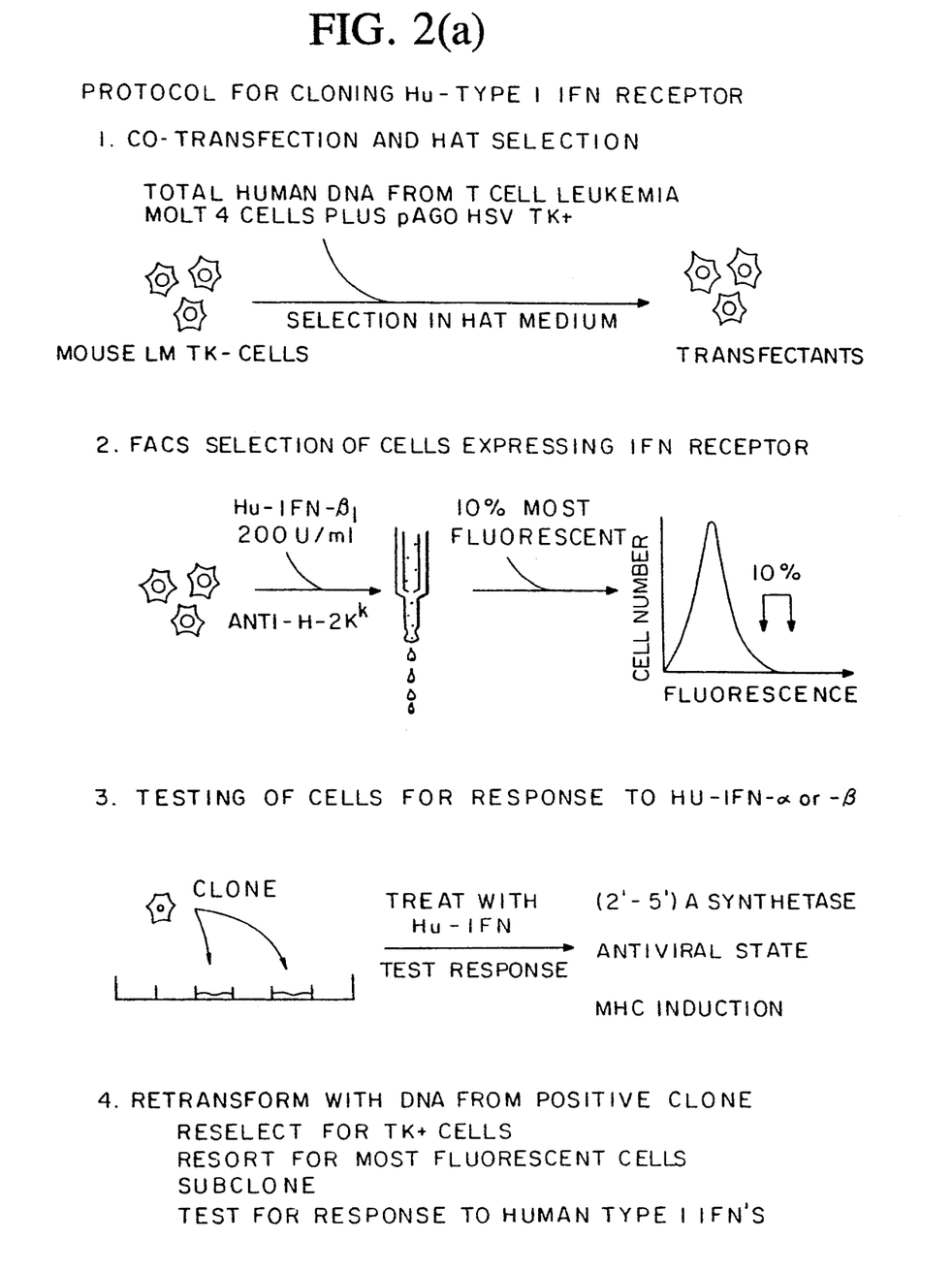
FIG. 2 is a schematic illustration of a preferred protocol for cloning proteins which modulate cellular response to Type I interferons, such proteins being putative components of the human Type I IFN receptor system.
Figure 2B:
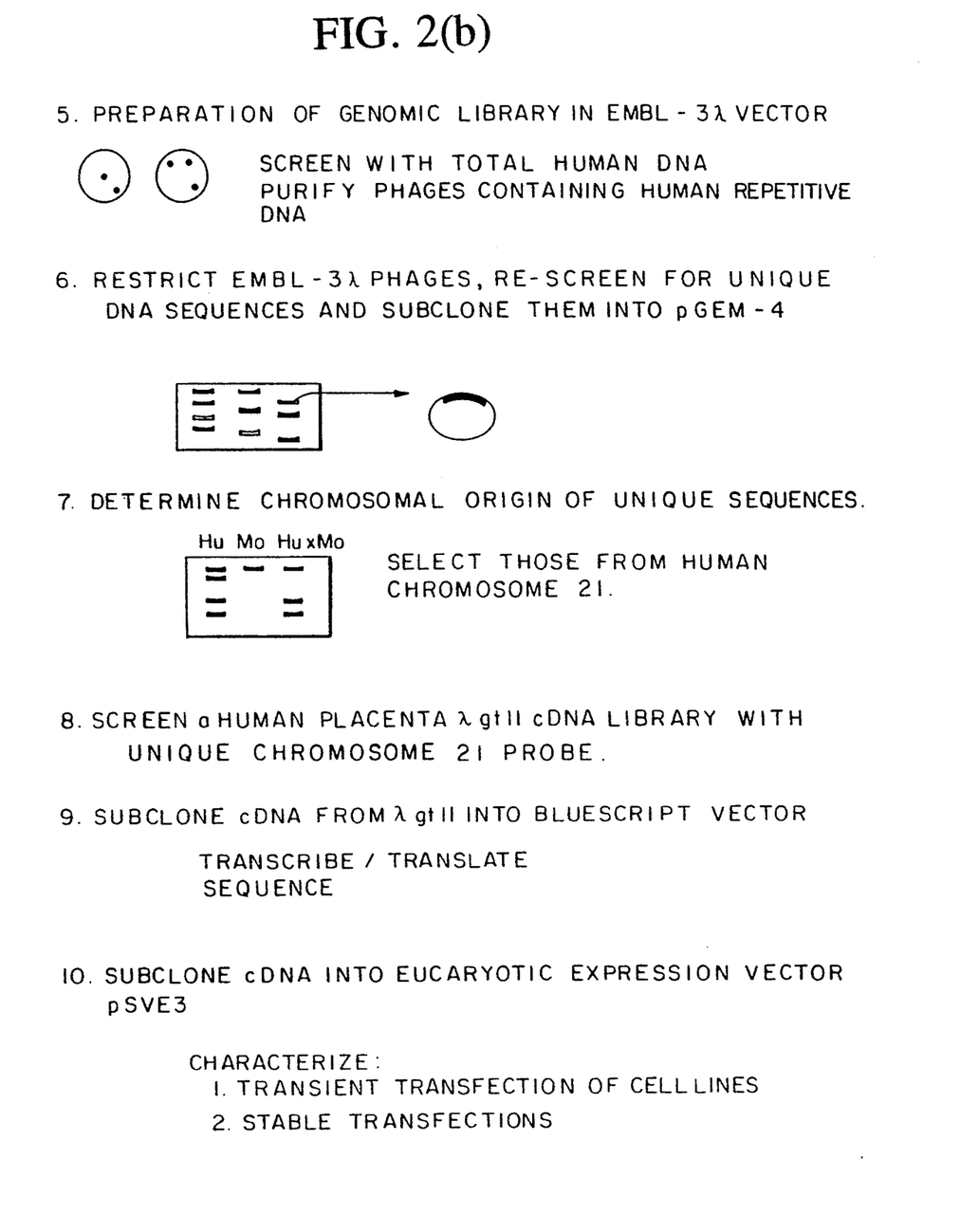
Figure 3:
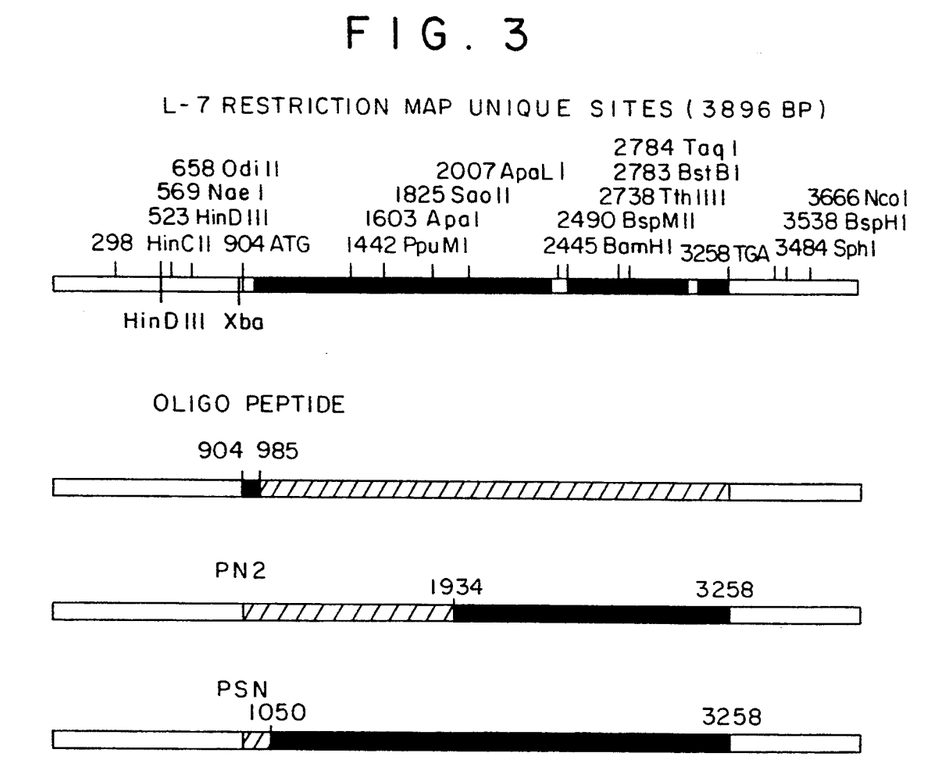
FIG. 3 is a restriction map of the L7 cDNA illustrating the structural relationship between three molecules used to raise antibodies, and the L7 protein.

A 27 amino acid long peptide near the aminoterminus of the L7 protein (FIG. 3), was synthesized, conjugated to KLH and used to raise rabbit antisera. The antibodies were purified on a column of immobilized peptide and used in Western blots. In Daudi and U937 cells a protein of 130 kDa is detected in Triton X-100-deoxycholate lysates and in membrane preparations. This is probably a glycosylated form of L7 which has an N-glycosylation site near the N-terminal region. However, immunoprecipitation was not possible with the peptide antibodies.

The L7 cDNA was fused through codon 113 to the protein A gene in vector pRIT-2 (Pharmacia Fine Chemicals) and expressed in *E. coli*. The fused protein PSN and PN2 (FIG. 3), purified on an immunoglobulin column, were used for immunization to obtain rabbit polyclonal antibodies to the L7 protein. These antibodies immunoprecipitated from human Daudi cells labelled for 7 hours with $^{35}$-methionine, major bands of 80–85 kDa and minor bands of about 130 kDa. The 80–85 kDa bands may be forms of the protein which have lost part of the N-terminal region recognized by the above anti-peptide antibody.

Figure 6:
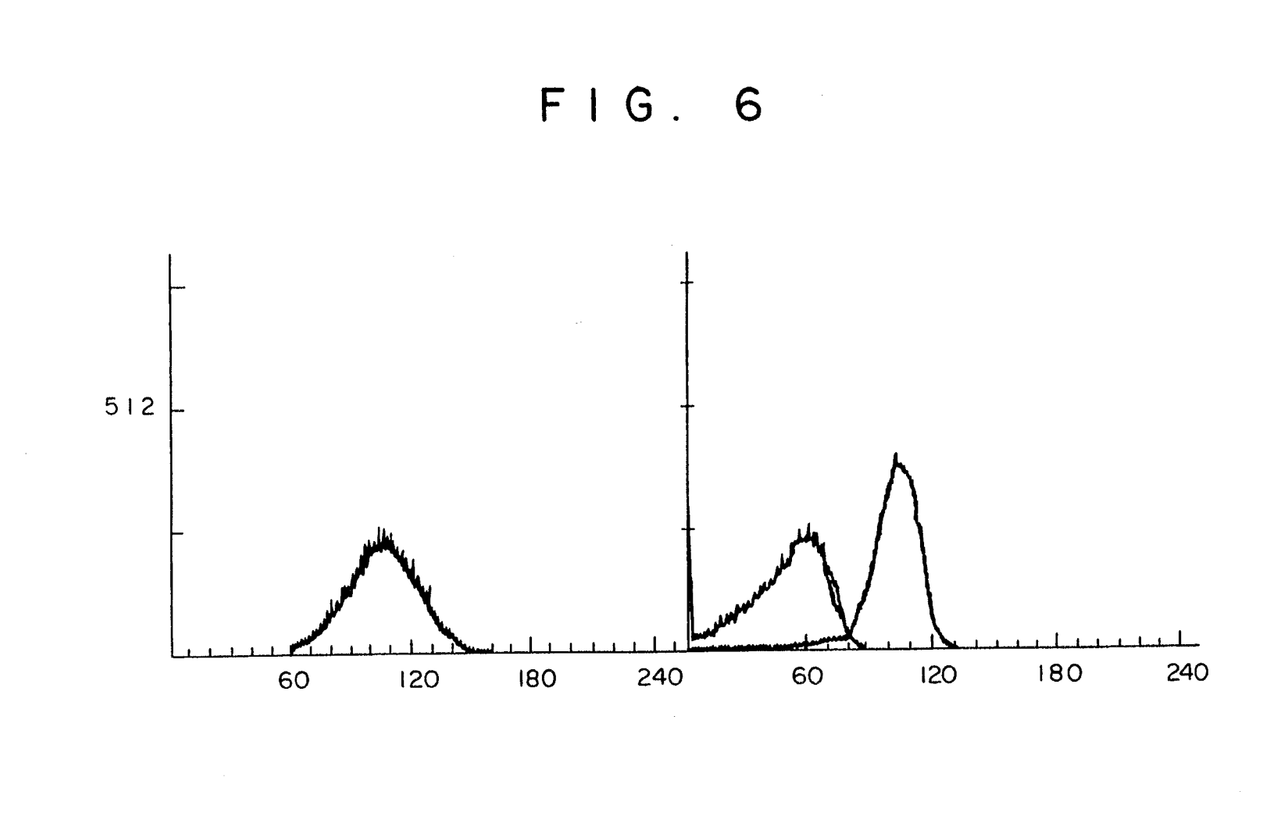
FIG. 6 is a FACS analysis of Daudi cells stained with Rhodamine-conjugated Protein A in the presence of rabbit anti-L7 (PSN) antibodies. The abscissa is fluorescence arbitrary units and the ordinate is the number of cells. The left panel is light scattering showing there are no differences in cell size with or without anti-L7. The right panel shows Rhodamine fluorescence: the two curves peaking at 60 are cells without rabbit antiserum or with normal (non-immune) rabbit serum; the curve peaking at 110 is from cells with anti-L7 antiserum. The displacement shows that all the Daudi cells have L7 on their surface.

With the rabbit antiserum against L7 (anti-PSN and PN2) it is possible to demonstrate that the L7 protein is on the surface of human lymphoblastoid cells (Daudi). FIG. 6 shows a fluorescence activated cell sorter (FACS) analysis demonstrating the presence of L7 on the surface of Daudi cells. The right panel shows that with Rhodamine isothiocyanate labeled protein A alone or with normal rabbit serum a peak of fluorescence is obtained at 60 arbitrary units. However, with added anti-L7 serum the peak of fluorescence is displaced to higher values (average 110) showing that the anti-L7 antibodies bind to the cells and hence more Rhodamine labelled Protein A is attached. The form of the curves shows that all the Daudi cells display the L7 protein on their surface.

Figure 7:
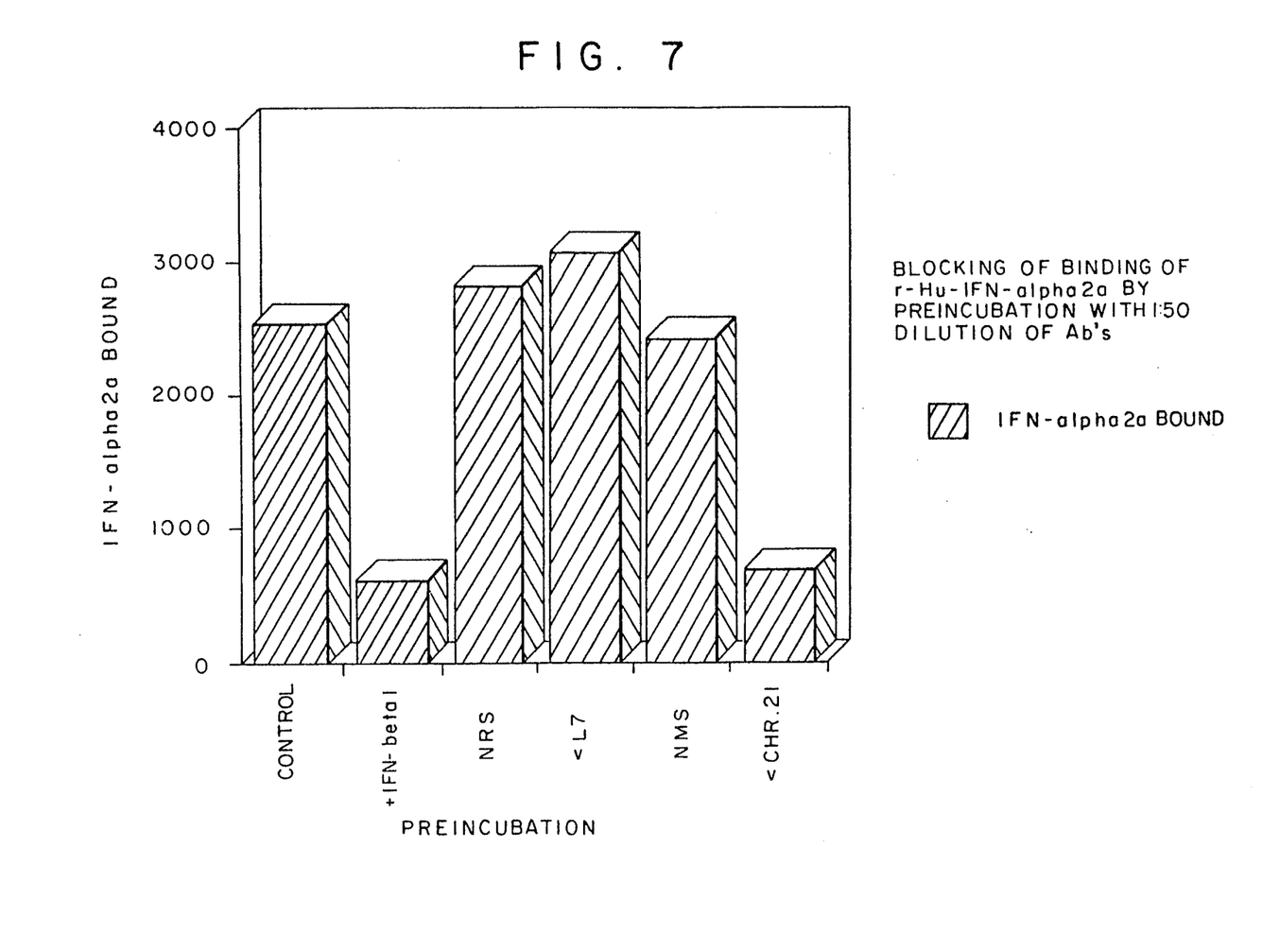
FIG. 7 is a bar graph showing the binding of human IFN-α to Daudi cells and the effect of different additions on this binding. Cold IFN-β competes, and so do antibodies to cells with chromosome 21 (<chr.21), but anti-L7 antibodies (<L7) do not inhibit. NRS and NMS are normal rabbit and mouse serum respectively.

The anti-L7 antibodies did not inhibit the binding of $^{125}$-IFN-$\alpha_2$ to human lymphoblastoid Daudi cells. FIG. 7 shows that the binding was inhibited by cold IFN-$\beta$, by antibodies against mouse-human hybrid cells containing only chromosome 21 (<chr.21), but not by anti-L7 (<L7), nor by normal rabbit serum (NRS) or normal mouse serum (NMS). Therefore, the L7 protein seems not to be directly involved i$_N$ the binding of IFN-$\alpha$ to these human cells. This would distinguish the L7 protein from the protein cross-linked to IFN-$\alpha$ on human cells (Razziudin et al, locus cited). It is not excluded that the protein which binds IFN-$\alpha$ may be different from that which binds IFN-$\beta$. Since the L7 protein was identified by its action on the response of cells to IFN-$\beta$, there has been an attempt to see if L7 could be cross-linked to IFN-$\beta$. Since radio-iodination of active IFN-$\beta$ was not successful, cold IFN-$\beta$ was cross-linked to Daudi cells by suberimidate treatment and the electrophoretic mobility of the L7 protein (detected by immunoblots with anti-peptide) was analyzed to determine if it decreased by this treatment. In one experiment, a slower 150 kDa band was observed in addition to the 130 kDa L7 protein, but two other experiments failed to show this phenomenon.

Conclusions

Identification of the L7 protein as a protein which modulates cellular response to Type I interferon and a component of the type I IFN receptor system is based on the following:

1. Transient expression of the L7 cDNA causes mouse cells to acquire a higher response to human IFN-$\beta$.
2. Stable transformants of hamster OHO cells with the L7 cDNA show an increased response to IFN. The increase is correlated with amplification of the integrated L7 DNA. The increased response is seen with human hamster IFN and is more marked at low concentrations of IFN, suggesting L7 augments the affinity of the cells to IFN.
3. The L7 protein is on the surface of human cells.
4. The gene encoding the L7 protein is on chromosome 21 in the region (q22) assigned to the type I receptor gene(s) by somatic cell genetics.

As in the case of other cytokines (e.g., IL-2, IFN-$\gamma$), the type I IFN receptor is probably formed by several different protein chains. The L7 protein is probably one component of the type I IFN receptor system and involved in the response of cells to IFN. It is probably not the chain of the receptor system which binds human IFN in a species specific way. It is more likely to be a chain of the receptor increasing the signal produced by the binding of IFN.

The identification of the L7 protein allows one to study its structure-function relationship, to produce a modified L7 protein with the aim of increasing or decreasing the response of cells, tissues and whole organisms to interferon of the $\alpha$ or $\beta$ type, and to produce by recombinant DNA technology soluble or lipid-bound L7 protein which can act as a competitor against IFN. These inventions can be applied to pathological situations in which one wishes to either enhance or to reduce the response to these types of interferons (e.g., autoimmune processes, chronic and acute infections, tumors and leukemias, etc.).

For example, L7 protein fragments. or analogues which interact with IFN, or antidiotypic antibodies raised against antibodies to the L7 protein, may be injected into a patient, acting as "decoys" for any interferon molecules present. Gene therapy with functional receptor genes can be used to provide more receptors and thereby increase the response to the IFN.

It should be understood that while a single specific protein, and the genetics material therefor, is described herein, the present invention is not limited thereto. The protocol for extracting genetic material coding for a protein which modulates cellular response to interferon has been shown to be effective by the experimental results described herein. Those of ordinary skill in this art will understand that if this protocol is repeated, different proteins also modulating cellular response to interferon, which proteins are likely to comprise the other chains of the Type I receptor system, may be obtained. While the protocol is specific to proteins which cause increased H2 antigen production, it is fully expected that additional proteins other than the specific one described herein will also have such properties and the present invention is intended to generically cover all of them.

Furthermore, the process of the present invention can also be repeated using other markers of interferon activity, e.g., other changes of cell surface characteristics caused by interferon, for detection of the interferon receptor system components. Such characteristics may include increased $\beta 2$ microglobulin or class II MHC antigens. When these techniques are used, proteins which modulate cellular response to interferon will also be obtained and such purified proteins and the genetic material encoding same are also part of the present invention.

It is known that any protein obtained in accordance with the present invention modulates cellular response to interferon. This is true by definition as it is that property which guides the selection of the genetic material. While it is thought that all such proteins are part of the interferon receptor system, applicant does not wish to be limited to such theory. It is known, however, that such proteins are not merely interferon inducers in view of their activity in responding to interferon, rather than creating it.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is tobe understood that the phraseology or terminology herein is for the purpose of description and not of limitation.

TABLE 1

Summary of Transient Transfections With pSVE3-L7
Increase in (2'–5') A synthetase by human IFN-$\beta_1$

| Cells | pSVE3-L7 | pSVE3 vector cpm | mock transfection |
|---|---|---|---|
| Balb/c | 700 (2.9)* | 240 (0.58)+ | 410 |
| Balb/c | 3720 (12.0) | 310 (1.00) | 310 |
| NIH 3T3 | 1430 (2.3) | 613 (1.1) | 530 |
| NIH 3T3 | 455 (3.9) | 115 | |
| NIH 3T3 | 540 (2.0) | 275 | |
| NIH 3T3 | 710 (4.4) | 160 (2.4) | 65 |
| NIH 3T3 | 417 (4.1) | 102 (1.3) | 76 |
| Mean | 1140 (4.5) | 260 (1.3) | 280 |

*Fold increase by pSVE3-L7 over pSVE3 vector alone in the response of transfected cells to human IFN-$\beta 1$ (500 U/ml).
+Fold increase of pSVE3 vector-transferred cells over non-transfected cells.

TABLE 2

(2'–5') A Synthetase Induction in CHO Cells
Transformed by pSVDHFR Alone (Control) or by pSVDHFR
and pSVE3-L7 cDNA. Amplified by 50 nM MTX

| CHO Transformed by Vector | Number of Clones Tested | (2'–5') A synthetase activity $-^{32}p$-(A2'p)$_n$A, cpm | | |
|---|---|---|---|---|
| | | No IFN | +Hu-IFN-$\beta$ | Induction |
| DHFR | 5 | 433 ± 109 | 1160 ± 433 | 727 ± 518 |
| DHFR + 7cDNA | 6 | 386 ± 105 | 3673 ± 931 | 3286 ± 884 |

Human IFN-$\beta$ used at 100 units/ml.

We claim:

1. Isolated DNA consisting essentially of nucleotides 899–3253 in FIG. 1 and which encodes a protein which induces increased 2'-5' oligosynthetase activity and increased H2-K$^k$ antigen expression in cell culture.

2. A recombinant vector comprising a DNA sequence in accordance with claim 1 and further comprising a promoter positioned in a way that expression of the protein encoded by said DNA sequence is possible.

3. A DNA vector in accordance with claim 2, wherein said promoter is the SV40 early promoter.

4. A cell comprising a transformed cell, transformed by a recombinant vector in accordance with claim 2, containing the genetic information imparted by said vector.

5. A non-human cell containing a human gene which includes the coding region 899–3253 of FIG. 1.

6. The isolated L7 protein encoded by the DNA of claim 1.

* * * * *